United States Patent
Jung et al.

(10) Patent No.: US 12,263,852 B2
(45) Date of Patent: Apr. 1, 2025

(54) SYSTEM AND METHOD FOR PREVENTING DRUNK DRIVING OF VEHICLE

(71) Applicant: HYUNDAI MOBIS CO., LTD., Seoul (KR)

(72) Inventors: Yu Jin Jung, Uiwang-si (KR); Yeon Su Kim, Gunpo-si (KR); June Seung Lee, Yongin-si (KR); Chang Won Lee, Seoul (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 288 days.

(21) Appl. No.: 17/873,298

(22) Filed: Jul. 26, 2022

(65) Prior Publication Data

US 2023/0044733 A1 Feb. 9, 2023

(30) Foreign Application Priority Data

Aug. 5, 2021 (KR) .......................... 10-2021-0103017

(51) Int. Cl.
*B60W 50/08* (2020.01)
*A61B 5/00* (2006.01)
(Continued)

(52) U.S. Cl.
CPC ........... *B60W 50/082* (2013.01); *A61B 5/082* (2013.01); *A61B 5/1172* (2013.01);
(Continued)

(58) Field of Classification Search
CPC ......... B60W 50/082; B60W 2420/403; B60W 2540/01; B60W 2540/043;
(Continued)

(56) References Cited

U.S. PATENT DOCUMENTS 3,818,434 A * 6/1974 Gotoh .................. B60K 28/063
340/576
6,970,075 B2 11/2005 Cherouny et al.
(Continued)

FOREIGN PATENT DOCUMENTS

KR 10-2004-0009435 A 1/2004

OTHER PUBLICATIONS

Extended EuropeanSearch Report issued on Dec. 23, 2022 in corresponding European patent application No. 22185890.5.

*Primary Examiner* — Donald J Wallace
*Assistant Examiner* — Jalal C Coduroglu
(74) *Attorney, Agent, or Firm* — Novo TechIP International PLLC

(57) ABSTRACT

Disclosed is a system for preventing drunk driving of a vehicle, the system including: an input unit through which a transfer intention to transfer a control privilege of a vehicle from a registered driver to a passenger is input; a sobriety determination unit configured to determine a current driver's inebriation state through a breathalyzer provided in the vehicle when the transfer intention is input through the input unit; a driver verification unit configured to identify personal information of the current driver seated on a driver's seat; and a control unit configured to transfer the control privilege of the vehicle to the passenger when the passenger is measured as being able to drive by the sobriety determination unit and the passenger and the current driver are identified to be the same by the driver verification unit.

13 Claims, 2 Drawing Sheets

(51) Int. Cl.
*A61B 5/08* (2006.01)
*A61B 5/1172* (2016.01)
*G06V 20/59* (2022.01)
*G06V 40/10* (2022.01)

(52) U.S. Cl.
CPC .......... *A61B 5/4845* (2013.01); *G06V 20/597* (2022.01); *G06V 40/10* (2022.01); *A61B 2503/22* (2013.01); *B60W 2420/403* (2013.01); *B60W 2540/01* (2020.02); *B60W 2540/043* (2020.02); *B60W 2540/225* (2020.02); *B60W 2540/24* (2013.01); *B60W 2710/18* (2013.01)

(58) Field of Classification Search
CPC ....... B60W 2540/225; B60W 2540/24; B60W 2710/18; B60W 2540/045; B60W 2540/227; B60W 40/08; B60W 10/18; B60W 50/0098; B60W 2040/0836; B60W 2040/0872; B60W 2040/0881; A61B 5/082; A61B 5/1172; A61B 5/4845; A61B 2503/22; G06V 20/597; G06V 40/10; B60K 28/063; B60K 28/06; G01N 33/4972
See application file for complete search history.

(56) References Cited

U.S. PATENT DOCUMENTS

| | | |
|---|---|---|
| 2004/0065564 A1* | 4/2004 | Casey ................. A44B 15/005 206/38 |
| 2008/0228365 A1 | 9/2008 | White et al. |
| 2009/0090577 A1* | 4/2009 | Takahashi .......... G01N 33/4972 340/576 |
| 2010/0152976 A1* | 6/2010 | White ............... A61B 5/14546 700/79 |
| 2010/0268425 A1* | 10/2010 | Pettersson ............ B60K 28/066 701/45 |
| 2010/0274411 A1* | 10/2010 | Ozaki .................. B60K 28/063 701/1 |
| 2012/0112897 A1 | 5/2012 | Oh et al. |
| 2012/0245763 A1* | 9/2012 | Mizuno ................ B60K 28/063 701/1 |
| 2014/0240086 A1* | 8/2014 | Van Wiemeersch ..... G05B 1/00 340/5.51 |
| 2015/0258892 A1* | 9/2015 | Wu ...................... G06V 40/166 340/576 |
| 2015/0360696 A1 | 12/2015 | Yi et al. |
| 2016/0318521 A1* | 11/2016 | Nothacker ............. A61B 5/082 |
| 2017/0096145 A1 | 4/2017 | Bahn |
| 2019/0011914 A1* | 1/2019 | Park ..................... B60W 40/09 |
| 2019/0286131 A1* | 9/2019 | Sasaki ...................... G08G 1/16 |
| 2020/0334983 A1* | 10/2020 | O'Sullivan ............ G06Q 10/02 |
| 2020/0377107 A1* | 12/2020 | Fung ..................... B60W 40/08 |
| 2021/0284202 A1* | 9/2021 | Furumoto ......... B60W 60/0053 |
| 2021/0290134 A1* | 9/2021 | Talamonti ................ A61B 5/37 |
| 2022/0234607 A1* | 7/2022 | Hata ..................... H04W 4/40 |

* cited by examiner

SYSTEM AND METHOD FOR PREVENTING DRUNK DRIVING OF VEHICLE

CROSS-REFERENCE TO RELATED APPLICATIONS

This application is based on and claims priority under 35 U.S.C. 119 to Korean Patent Application No. 10-2021-0103017, filed on Aug. 5, 2021, in the Korean Intellectual Property Office, the disclosure of which is incorporated herein by reference in its entirety.

TECHNICAL FIELD

The disclosure relates to a system and method for preventing drunk driving of a vehicle and, more particularly, to a technology for transferring the control right of a vehicle (i.e., vehicle control privilege) to a passenger and allowing the passenger to drive the vehicle in a case where a driver registered in the vehicle is inebriated.

BACKGROUND

Recently, automobiles have been established as necessities of life, and the number of the automobiles is rapidly increasing. In order to drive a vehicle safely, the driver must be conscious of safety above all else, and an example of an accident caused by a lack of this safety awareness is a drunk driving accident.

Drunk driving not only causes bodily injury and property damage, but also jeopardizes the lives of others, and thus requires special measures. As drunk driving has emerged as a serious social problem, the penalties for drunk driving are being strengthened.

In order to prevent such drunk driving, strong legal sanctions are imposed on drivers, and recently a law that punishes the person in the passenger seat if an accident occurs due to the driver driving while inebriated has come into effect, but this was insufficient to prevent drunk driving accidents.

Although a breathalyzer tester for drivers has been recently released, a driver himself or herself can drive a vehicle while ignoring the measurement result of such a tester. In this case, the tester could only perform the role of a simple tester without fundamentally preventing drunk driving.

In addition, a conventional car does not have a separate device that rejects the driver's attempt to drive the car while the driver is inebriated, so it was not possible to prevent drunk driving. Police checks of drivers for inebriation causes various inconveniences and inefficiencies.

Due to this, in the prior art, an invention in which a breathalyzer is provided in a vehicle has been proposed, but when a passenger attempts to drive a car instead of the registered driver because the driver is inebriated, there is a problem that the control privilege of the vehicle is not transferred to the passenger.

It should be noted that the information disclosed in the above background section is only for enhancing the understanding of the background of the disclosure, and therefore may include information that does not constitute prior art known to those of ordinary skill in the art.

SUMMARY

The disclosure has been made in order to solve the above-mentioned problems in the prior art and an aspect of the disclosure is to input the intention to transfer the control right of a vehicle or a vehicle control privilege by a registered driver, detect the inebriation state of a passenger, and to transfer the control right to the passenger by identifying that the passenger is a current driver.

In accordance with an aspect of the disclosure, a system for preventing drunk driving of a vehicle may include: an input unit through which a transfer intention to transfer a control right of a vehicle from a registered driver to a passenger is input; a sobriety determination unit configured to determine a current driver's inebriation state through a breathalyzer provided in the vehicle when the transfer intention is input through the input unit; a driver verification unit configured to identify personal information of the current driver seated on a driver's seat; and a control unit configured to transfer the control right of the vehicle to the passenger when the passenger is measured as being able to drive by the sobriety determination unit and the passenger and the current driver are identified to be the same by the driver verification unit.

The input unit allows inputting of the transfer intention to transfer the control right of the vehicle to the passenger when personal information of a vehicle's owner is identified by the driver verification unit.

The driver verification unit may be connected to a personal identification sensor provided in the vehicle to identify the personal information, and the personal identification sensor may include a camera sensor or a fingerprint recognition sensor provided in the vehicle.

The driver verification unit may identify the current driver at predetermined periods or continuously.

The system for preventing drunk driving of the vehicle may further include a driver status monitoring unit configured to detect a current driver's grip on a steering wheel or a forward gaze state of the current driver, wherein the control unit may identify that the passenger is the current driver by the driver verification unit, and may transfer the control right of the vehicle to the passenger when it is identified that the current driver looks ahead while gripping the steering wheel by the driver status monitoring unit.

The breathalyzer may measure a blood alcohol level through the driver's breath, and the sobriety determination unit may determine that the current driver is inebriated when the measured blood alcohol level is greater than or equal to a reference value.

When the blood alcohol level less than the reference value is detected by the sobriety determination unit upon transferring the control right, the control unit may control the vehicle to travel in a safety mode in which a preload is generated in a brake of the vehicle or sensitivity of an external detection sensor of the vehicle is improved.

In accordance with another aspect of the disclosure, a method for preventing drunk driving of a vehicle may include: inputting a transfer intention to transfer a control right of a vehicle from a registered driver to a passenger; determining a current driver's inebriation state through a breathalyzer provided in the vehicle when the transfer intention is input in the inputting of the transfer intention; identifying personal information of the current driver seated on a driver's seat; and transferring the control right of the vehicle to the passenger when the passenger is determined to be able to drive in the determining of the inebriation state and when the passenger and the current driver are identified to be the same in the identifying of the personal information of the current driver.

The method for preventing drunk driving of the vehicle may further include identifying personal information of a registered driver before the inputting of the transfer intention.

The identifying of the personal information of the current driver may include identifying the personal information in conjunction with a personal identification sensor provided in the vehicle, and the personal identification sensor may include a camera sensor or fingerprint recognition sensor provided in the vehicle.

The method for preventing drunk driving of the vehicle may further include detecting a current driver's grip on a steering wheel or a forward gaze state of the current driver after the identifying of the personal information of the current driver, wherein the transferring of the control right may include transferring the control right of the vehicle to the passenger when the current driver looks ahead while gripping the steering wheel in the detecting of the current driver's grip.

The determining of the inebriation state may further include measuring a blood alcohol level of the current driver through a breathalyzer provided in the vehicle, and determining the inebriation state of the current driver by comparing the measured blood alcohol level with a reference value.

The method for preventing drunk driving of the vehicle may further include, when the blood alcohol level less than the reference value is detected in the determining of the inebriation state, controlling the vehicle to travel in a safety mode in which a preload is generated in a brake of the vehicle or sensitivity of an external detection sensor of the vehicle is improved, after the transferring of the control right.

In the system for preventing drunk driving of the vehicle according to the disclosure, when a registered driver is inebriated and transfers the control right of a vehicle to a passenger, the system monitors continuous seating of the passenger on the driver's seat, so as to prevent the passenger from taking a sobriety test in place of the inebriated driver and prevent the registered driver from driving while inebriated, and allows the passenger to receive the transferred control right and drive the vehicle, thereby preventing drunk driving.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
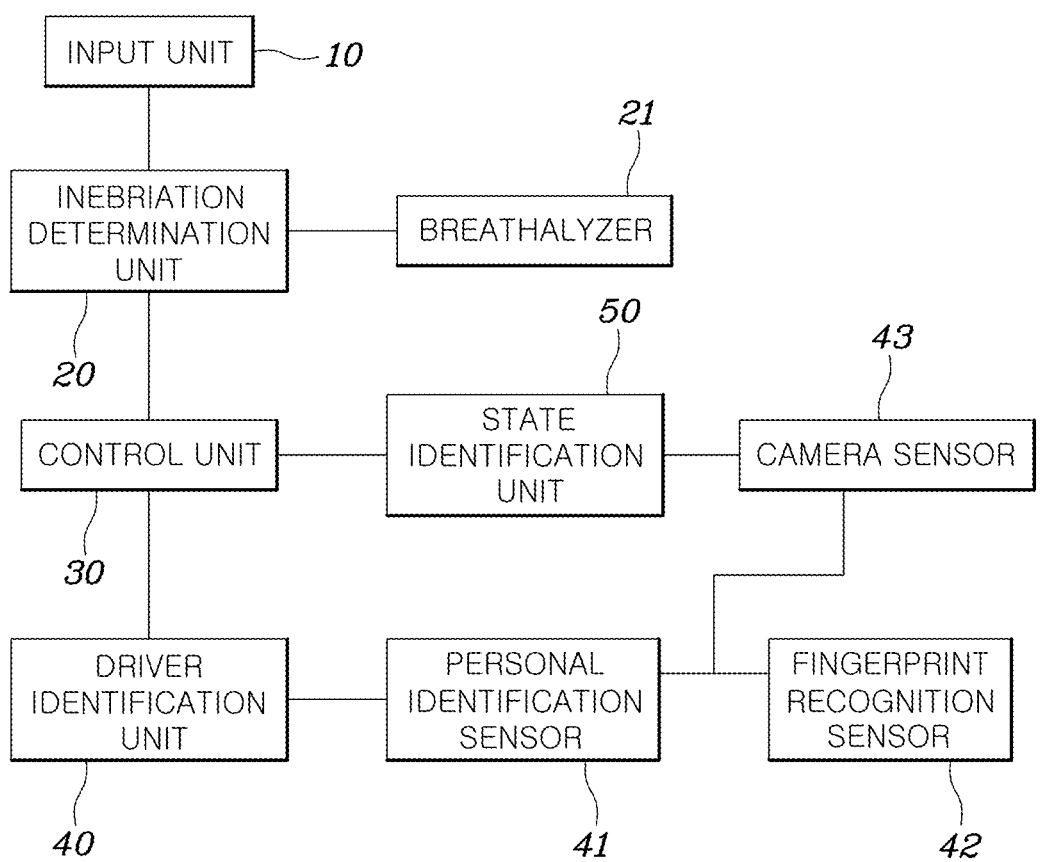
FIG. 1 is a configuration diagram illustrating a system for preventing drunk driving of a vehicle according to an embodiment of the disclosure.

A specific structural or functional description of embodiments of the present disclosure set forth in the specification or application is given merely for the purpose of describing the embodiment according to the present disclosure. Therefore, the embodiments according to the present disclosure may be implemented in various forms, and the present disclosure should not be construed as being limited to the embodiments described in the specification or application.

Various changes and modifications may be made to the embodiments according to the present disclosure, and therefore particular embodiments will be illustrated in the drawings and described in the specification or application. However, it should be understood that embodiments according to the concept of the present disclosure are not limited to the particular disclosed embodiments, but the present disclosure includes all modifications, equivalents, and alternatives falling within the spirit and scope of the present disclosure.

Such terms as "a first" and/or "a second" may be used to describe various elements, but the elements should not be limited by these terms. These terms are intended merely to distinguish one element from other elements. For example, a first element may be named a second element and similarly a second element may be named a second element without departing from the scope of protection of the present disclosure.

In the case where an element is referred to as being "connected" or "accessed" to other elements, it should be understood that not only the element is directly connected or accessed to the other elements, but also another element may exist between them. Contrarily, in the case where a component is referred to as being "directly connected" or "directly accessed" to any other component, it should be understood that there is no component therebetween. The other expressions of describing a relation between structural elements, i.e., "between" and "merely between" or "neighboring" and "directly neighboring", should be interpreted similarly to the above description.

The terms used in the present disclosure are merely used to describe specific embodiments, and are not intended to limit the present disclosure. A singular expression may include a plural expression unless they are definitely different in a context. As used herein, the expression "include" or "have" are intended to specify the existence of mentioned features, numbers, steps, operations, elements, components, or combinations thereof, and should be construed as not precluding the possible existence or addition of one or more other features, numbers, steps, operations, elements, components, or combinations thereof.

Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure.

Hereinafter, exemplary embodiments of the present disclosure will be described in detail with reference to the accompanying drawings. Similar or like reference signs presented in the respective drawings designate similar or like elements.

An input unit 10, a sobriety determination unit 20, a control unit 30, a driver verification unit 40, and a driver status monitoring unit 50 according to an exemplary embodiment of the disclosure may be implemented through a processor (not shown) configured to perform operations described below by using a nonvolatile memory (not shown) configured to store an algorithm configured to control the operations of various components of a vehicle or data relating to software instructions for reproducing the algorithm and data stored in the memory. Here, the memory and the processor may be implemented as a separate chip, respectively. Alternatively, the memory and processor may be implemented as a single chip integrated with each other. The processor may have a form of one or more processors.

FIG. 1 is a configuration diagram illustrating a system for preventing drunk driving of a vehicle according to an embodiment of the disclosure.

A preferred embodiment of the system for preventing drunk driving of a vehicle according to the disclosure will be described with reference to FIG. 1.

The vehicle may be provided with a breathalyzer 21 to identify an inebriation state of a driver before the operation of the vehicle to prevent drunk driving of the driver.

The breathalyzer 21 may be provided in the same form as the conventional breathalyzer 21 and may measure the driver's blood alcohol level through the driver's breath, and the measured information may be transmitted to the vehicle's system.

The disclosure is designed to transfer the control right of a vehicle to a passenger who is not inebriated while a previously registered driver of the vehicle is inebriated.

A system for preventing drunk driving of a vehicle may include an input unit 10 through which a transfer intention to transfer a control right of a vehicle from a registered driver to a passenger is input; a sobriety determination unit 20 configured to determine a current driver's inebriation state through a breathalyzer 21 provided in the vehicle when the transfer intention is input through the input unit 10; a driver verification unit 40 configured to identify personal information of the current driver seated on a driver's seat; and a control unit 30 configured to transfer the control right of the vehicle to the passenger when the passenger is measured as being able to drive by the sobriety determination unit 20 and the passenger and the current driver are identified to be the same by the driver verification unit 40.

In order to transfer the control right of a vehicle to a passenger in a state where a driver registered in a control system of the vehicle cannot drive while being inebriated, the driver may input an intention to transfer the control right through the input unit 10, and the input unit 10 is connected to a system operation device of the vehicle including a jog module or a touch screen provided in the vehicle so that the registered driver can transfer all control rights related to the operation of the vehicle to the passenger.

The blood alcohol level of the current driver seated on the driver's seat may be measured by the breathalyzer 21 provided adjacent to the driver's seat of the vehicle, and the sobriety determination unit 20 may determine the driver's inebriation state based on the current driver's blood alcohol level measured by the breathalyzer 21.

The driver verification unit 40 may verify an identity of a driver currently seated at the driver's seat. For example, the driver verification unit 40 may identify that the passenger seated on the driver's seat is not the registered driver but a passenger who is determined to be in a non-inebriation state by the sobriety determination unit 20 through a personal identification sensor 41 provided in the vehicle, so that the passenger may take a breathalyzer test instead of the registered driver who is inebriated, thereby preventing the registered driver from driving under the influence of alcohol.

When it is identified by the driver verification unit 40 that the current driver is not the registered driver but the passenger who has taken the breathalyzer test, the control unit 30 may transfer the control right to the passenger so that the passenger can control the driving of the vehicle.

Through this, there is an effect that can prevent drunk driving as the registered driver transfers the control right of the vehicle to the passenger when the passenger drives the vehicle due to inebriation of the driver.

The input unit 10 allows inputting of a transfer intention to transfer the control right of the vehicle to the passenger when personal information of a vehicle's owner is identified by the driver verification unit 40.

In order to prevent theft of the vehicle, the personal information of the registered driver may be identified by the driver verification unit 40, and then the transfer intention to transfer the control right may be input through the input unit 10.

This configuration can prevent another person other than the driver registered in the input unit 10 from inputting the transfer intention to transfer the control right.

The driver verification unit 40 may be connected to a personal identification sensor 41 provided in the vehicle to identify the personal information, and the personal identification sensor 41 may include a camera sensor 43 or a fingerprint recognition sensor 42 provided in the vehicle.

The personal identification sensor 41 may include the camera sensor 43 or the fingerprint recognition sensor 42 provided adjacent to the driver's seat. Here, the camera sensor 43 mounted adjacent to the driver's seat may recognize the personal information by capturing the current driver's face or iris or may recognize the current driver's fingerprint through the fingerprint recognition sensor 42 mounted adjacent to a steering wheel or the driver's seat.

The driver verification unit 40 may periodically or continuously identify the current driver.

The identification of the current driver may be performed in the same way as a breathalyzer sensor, and the current driver may be recognized continuously or at predetermined periods, thereby preventing others from taking breathalyzer tests on behalf of the current driver.

The system for preventing drunk driving of the vehicle may further include the driver status monitoring unit 50 configured to detect a current driver's grip on a steering wheel or a forward gaze state of the current driver. The control unit 30 may identify that the passenger is the current driver by the driver verification unit 40, and the driver status monitoring unit 50 may transfer the control right of the vehicle to the passenger when the current driver looks ahead while gripping the steering wheel.

In order to prevent the passenger from taking the breathalyzer test instead of the driver and to prevent drunk driving of the driver, the driver status monitoring unit 50 may identify that the current driver is gripping the steering wheel and continuously looking ahead.

The driver status monitoring unit 50 may identify the forward gaze of the current driver through the camera sensor 43 provided in the vehicle or may identify the grip on the steering wheel through a pressure sensor provided on the steering wheel, and may identify the grip on the steering wheel and continuous forward gaze through various sensors.

The breathalyzer 21 may measure the blood alcohol level through the driver's breath, and the sobriety determination unit 20 may determine that the current driver is inebriated when the measured blood alcohol level is greater than or equal to a reference value.

The breathalyzer 21 may measure the blood alcohol level by suctioning the breath, and the sobriety determination unit 20 may determine that driving is possible when the measured blood alcohol level is less than the reference value and that driving is impossible when the measured blood alcohol level is greater than or equal to the reference value by comparing the measured blood alcohol level with the reference value.

When the blood alcohol level less than the reference value is detected by the sobriety determination unit 20 upon transferring the control right, the control unit 30 may control the vehicle to travel in a safety mode in which a preload is generated in a brake of the vehicle or sensitivity of an external detection sensor of the vehicle is improved.

Although it is determined by the sobriety determination unit 20 that the passenger can drive the vehicle, when the blood alcohol level is lower than the reference value, but is detected even a little, driving may be dangerous, and the control unit 30 may control the vehicle in the safety mode.

The safety mode has the effect of improving the sensitivity of an external collision detection sensor of the vehicle or generating a preload of the brake to prepare for a vehicle collision.

Figure 2:
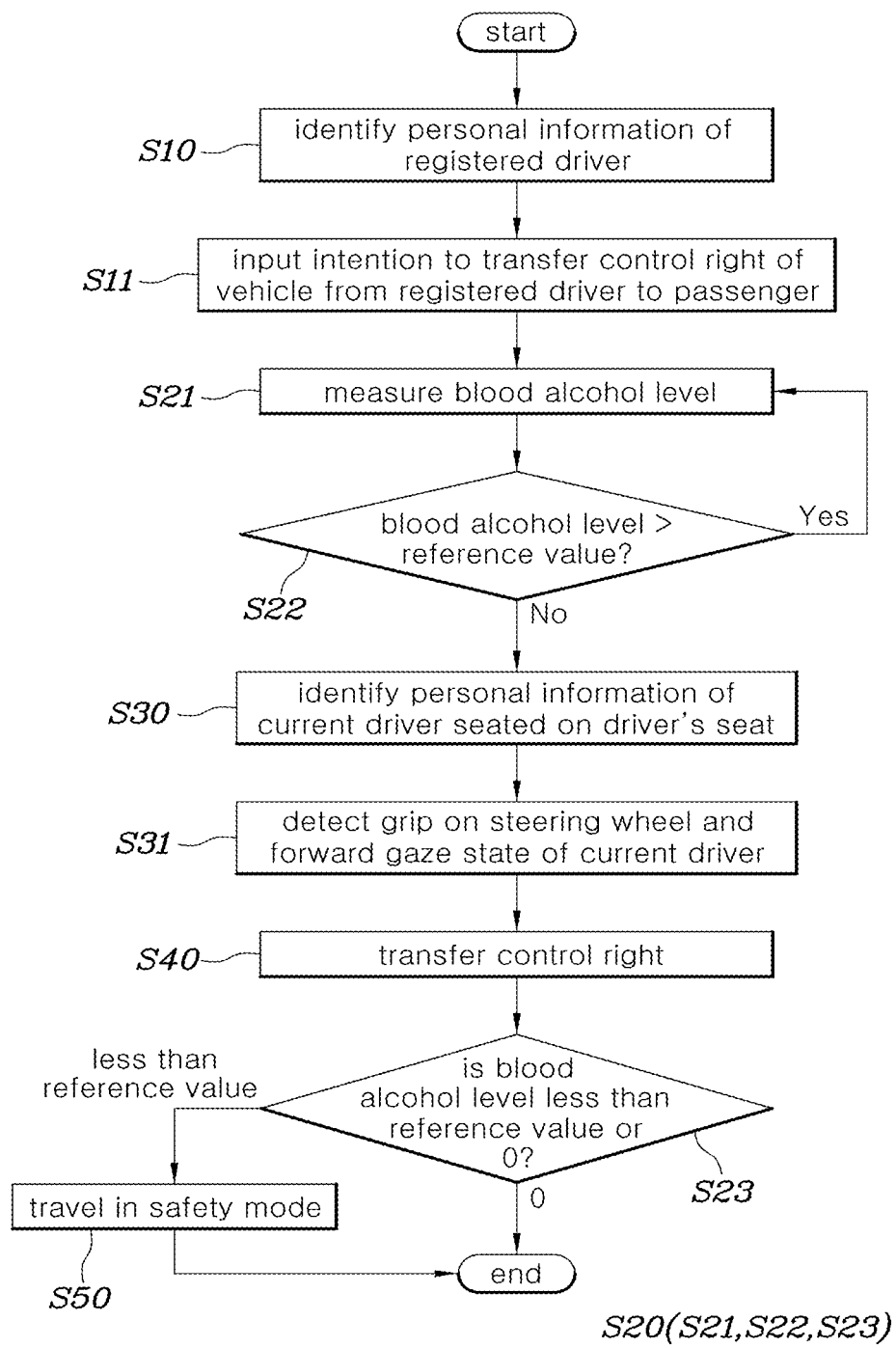
FIG. 2 is a flowchart illustrating a method for preventing drunk driving of a vehicle according to an embodiment of the disclosure.

FIG. 2 is a flowchart illustrating a method for preventing drunk driving of a vehicle according to an embodiment of the disclosure.

A preferred embodiment of a method for preventing drunk driving of a vehicle according to the disclosure will be described with reference to FIG. 2.

The method for preventing drunk driving of the vehicle according to the disclosure may include inputting (S11) a transfer intention to transfer a control right of a vehicle from a registered driver to a passenger; determining (S20) a current driver's inebriation state through a breathalyzer 21 provided in the vehicle when the transfer intention is input in the inputting (S10) of the transfer intention; identifying (S30) personal information of the current driver seated on a driver's seat; and transferring (S40) the control right of the vehicle to the passenger when the passenger is determined to be able to drive in the determining (S20) of the inebriation state and when the passenger and the current driver are identified to be the same in the identifying (S30) of the personal information of the current driver.

The method for preventing drunk driving of the vehicle according to the disclosure may further include identifying (S10) personal information of the registered driver before the inputting (S11) of the transfer intention.

The identifying (S30) of the personal information of the current driver may include identifying the personal information in conjunction with a personal identification sensor 41 provided in the vehicle, and the personal identification sensor 41 may include a camera sensor 43 or fingerprint recognition sensor 42 provided in the vehicle.

The method for preventing drunk driving of the vehicle according to the disclosure may further include detecting (S31) a current driver's grip on a steering wheel or a forward gaze state of the current driver after the identifying (S30) of the personal information of the current driver, and the transferring of the control right may include transferring the control right of the vehicle to the passenger when the current driver looks ahead while gripping the steering wheel in the detecting of the current driver's grip.

The determining (S20) of the inebriation state may further include measuring (S21) a blood alcohol level of the current driver through a breathalyzer 21 provided in the vehicle, and determining (S21) whether the current driver is inebriated by comparing the measured blood alcohol level with a reference value.

The method for preventing drunk driving of the vehicle according to the disclosure may further include, when the blood alcohol level less than the reference value is detected (S23) in the determining (S20) of the inebriation state, controlling (S50) the vehicle to travel in a safety mode in which a preload is generated in a brake of the vehicle or sensitivity of an external detection sensor of the vehicle is improved, after the transferring (S40) of the control right.

Although the present disclosure has been described and illustrated in conjunction with particular embodiments thereof, it will be apparent to those skilled in the art that various improvements and modifications may be made to the present disclosure without departing from the technical idea of the present disclosure defined by the appended claims.

What is claimed is:

1. A system for preventing drunk driving of a vehicle including a breathalyzer, the system comprising:
   an input unit configured to receive, from a driver registered to the system, an intention to transfer a vehicle control privilege from the registered driver to a passenger;
   a sobriety determination unit configured to determine, in response to the input unit receiving the intention to transfer, an inebriation of a current driver seated at a driver's seat of the vehicle, using the breathalyzer;
   a driver verification unit configured to verify an identity of the current driver; and
   a control unit configured to transfer the vehicle control privilege to the passenger in response to (1) the sobriety determination unit determining that the current driver is not inebriated, and (2) the driver verification unit verifying that the identity of the current driver corresponds to the passenger.

2. The system of claim 1, wherein the driver verification unit is configured to verify an identity of the registered driver before the input unit receives the intention to transfer the vehicle control privilege.

3. The system of claim 1, further comprising an identification sensor disposed at the vehicle and configured to detect identification information of the passenger, wherein:
   the driver verification unit is configured to receive, from the identification sensor, the identification information of the passenger, and verify the identity of the passenger based on the received identification information, and
   the identification sensor comprises a camera or fingerprint sensor.

4. The system of claim 1, wherein the driver verification unit is configured to periodically or continuously verify the identity of the current driver.

5. The system of claim 1, further comprising a driver status monitoring unit configured to detect a grip of the current driver on a steering wheel of the vehicle or a forward gazing status of the current driver,
   wherein the control unit is configured to:
      receive, from the driver status monitoring unit, driver status information indicating the grip of the current driver on the steering wheel or the forward gazing status of the current driver;
      determine, based on the received driver status information, a driver status of the current driver; and
      in response to the determined driver status indicating that the current driver is looking ahead or gripping the steering wheel, transfer the vehicle control privilege to the passenger.

6. The system of claim 1, wherein:
   the breathalyzer is configured to measure a blood alcohol level from a breath of the current driver, and
   for determining the inebriation of the current driver, the sobriety determination unit is configured to determine whether the measured blood alcohol level of the current driver is equal to or greater than a reference value.

7. The system of claim 6, wherein:
   in response to the sobriety determination unit determining that the measured blood alcohol level is less than the reference value, the control unit is configured to operate the vehicle to travel in a safety mode, and the vehicle is configured to, when operated in the safety mode, generate a preload in a brake of the vehicle or increase a sensitivity of a collision detection sensor of the vehicle.

8. A method for preventing drunk driving of a vehicle, comprising:

receiving, via a user input unit of the vehicle, a user input from a driver registered to the system, the user input including an intention of the registered driver to transfer a vehicle control privilege from the registered driver to a passenger;

in response to receiving the intention to transfer, performing:

determining, using a breathalyzer disposed at the vehicle, an inebriation of a current driver seated at a driver's seat of the vehicle; and verifying an identity of the current driver; and in response to (1) determining that that the verified identity of the current driver corresponds to the passenger and (2) determining, based on the determined inebriation of the current driver, that the passenger is not inebriated, transferring the vehicle control privilege to the passenger.

9. The method of claim 8, further comprising verifying an identification of the registered driver before receiving the intention to transfer the vehicle control privilege.

10. The method of claim 8, wherein:

verifying the identity of the current driver comprises detecting, using a personal identification sensor disposed at the vehicle, identification information of the current driver, and the personal identification sensor comprises a camera or fingerprint sensor.

11. The method of claim 8, further comprising, in response to verifying the identity of the current driver, detecting a grip of the current driver on a steering wheel of the vehicle or a forward gazing status of the current driver, wherein transferring the vehicle control privilege to the passenger comprises transferring the vehicle control privilege to the passenger in response to detecting that the current driver is looking ahead or gripping the steering wheel.

12. The method of claim 8, wherein determining the inebriation of the current driver comprises:

measuring, using the breathalyzer, a blood alcohol level of the current driver; and determining whether the measured blood alcohol level is equal to or higher than a reference value.

13. The method of claim 12, further comprising, in response to determining that the measured blood alcohol level is less than the reference value, controlling the vehicle to travel in a safety mode, wherein the vehicle is configured to, when travelling in the safety mode, generate a preload in a brake of the vehicle or increase a sensitivity of a collision detection sensor of the vehicle.

* * * * *